US012583760B2

(12) United States Patent
Song et al.

(10) Patent No.: US 12,583,760 B2
(45) Date of Patent: Mar. 24, 2026

(54) WATER PURIFIER

(71) Applicant: COWAY CO., LTD.,
Chungcheongnam-do (KR)

(72) Inventors: Min Su Song, Chungcheongnam-do
(KR); Hyun Suk Moon,
Chungcheongnam-do (KR); **Si Jun
Park**, Chungcheongnam-do (KR);
Chang Seob Yeom,
Chungcheongnam-do (KR)

(73) Assignee: COWAY CO., LTD.,
Chungcheongnam-do (KR)

( * ) Notice: Subject to any disclaimer, the term of this
patent is extended or adjusted under 35
U.S.C. 154(b) by 676 days.

(21) Appl. No.: 17/975,802

(22) Filed: Oct. 28, 2022

(65) Prior Publication Data

US 2023/0278890 A1 Sep. 7, 2023

(30) Foreign Application Priority Data

Mar. 4, 2022 (KR) ........................ 10-2022-0028200

(51) Int. Cl.
C02F 1/00 (2023.01)
A61L 2/10 (2006.01)
A61L 2/26 (2006.01)

(52) U.S. Cl.
CPC ................ C02F 1/003 (2013.01); A61L 2/10
(2013.01); A61L 2/26 (2013.01); *A61L
2202/11* (2013.01);
(Continued)

(58) Field of Classification Search
None
See application file for complete search history.

(56) References Cited

U.S. PATENT DOCUMENTS 5,160,173 A * 11/1992 Le Devehat ............. B67D 7/78
285/364
2016/0229716 A1 8/2016 Lee et al.
(Continued)

FOREIGN PATENT DOCUMENTS

CN 213834904 U * 7/2021
JP 2020517540 A 6/2020
(Continued)

OTHER PUBLICATIONS

"JP Application 2022-172980", Office Action Mailed Nov. 7, 2023,
Nov. 7, 2023, 4 pgs.
(Continued)

*Primary Examiner* — Bradley R Spies
*Assistant Examiner* — Jeannie McDermott
(74) *Attorney, Agent, or Firm* — Guntin & Gust, PLC;
Miyoung Shin

(57) ABSTRACT

A water purifier includes a water purification module that
filters raw water to generate purified water, and a water
outlet module that receives the purified water and outputs
the purified water to the outside. The water outlet module
includes a housing, a purified water inlet flow path of which
at least a portion is disposed inside the housing and into
which the purified water is introduced, a movable part
displaced between a first position in which the movable part
is retracted into the housing and a second position in which
the movable part is extracted to a front side of the housing,
a driving part that displaces the movable part, and a water
outlet part that includes a plurality of link water outlet flow
paths rotatably connected to each other and is connected to
the movable part to receive the purified water and discharge
the purified water to an outside.

10 Claims, 10 Drawing Sheets

230 : 231, 232
240 : 241, 242, 243, 244, 245
250 : 250a, 250b, 250c, 250d, 250e, 250f, 250g

(52) U.S. Cl.
CPC .... *C02F 2201/002* (2013.01); *C02F 2303/04* (2013.01)

(56) References Cited

U.S. PATENT DOCUMENTS

| | | | | |
|---|---|---|---|---|
| 2020/0384390 A1* | 12/2020 | Lee | ........................ | B01D 35/04 |
| 2021/0017009 A1* | 1/2021 | Jung | .................... | B67D 1/0894 |
| 2022/0290418 A1* | 9/2022 | Dombrowsky | ......... | E03C 1/182 |

FOREIGN PATENT DOCUMENTS

| | | | | | |
|---|---|---|---|---|---|
| KR | 20120070286 A | * | 6/2012 | ......... | B01D 35/1573 |
| KR | 20180063657 A | | 6/2018 | | |
| KR | 102064180 B1 | | 1/2020 | | |
| KR | 20210096346 A | | 8/2021 | | |

OTHER PUBLICATIONS

"[Coway x BTS] Premium Design Coway Noble Water Purifier, Select Your Color and Your Style", https://www.youtube.com/watch?v=aVAWuyVYOV0, posted on Feb. 25, 2022 (accessed on Jan. 13, 2023).
"[Coway x BTS] Brand New Premium Design Wafer Purifier | Minimal Design Series" https://www.youtube.com/watch?v=znz2OZoDrGs, Posted on Jan. 12, 2022 (Accessed on Jan. 17, 2023).
"[Coway x BTS] Premium Design Water Purifier Coway Noble", https://www.youtube.com/watch?v=8tihvQ6M7fs, posted on Jan. 25, 2022 (accessed on Jan. 13, 2023).
"[Coway x BTS] Premium Design Water Purifier Implementing Complete Built-In Structure | Noble Water Purifier", https://www.youtube.com/watch?v=piTu6S3V35U, posted on Nov. 26, 2021 (accessed on Jan. 13, 2023, Nov. 26, 2021.
"Coway launches Noble Water Purifier", English Translation Included, earliest document date Oct. 29, 2021, 20 pgs.

* cited by examiner

230 : 231, 232
240 : 241, 242, 243, 244, 245
250 : 250a, 250b, 250c, 250d, 250e, 250f, 250g

230 : 231, 232
240 : 241, 242, 243, 244, 245
250 : 250a, 250b, 250c, 250d, 250e, 250f, 250g

WATER PURIFIER

CROSS-REFERENCE TO RELATED APPLICATION

This application claims priority to and the benefit of Korean Patent Application No. 10-2022-0028200 filed on Mar. 4, 2022, the disclosure of which is incorporated herein by reference in its entirety.

BACKGROUND

1. Field

The present disclosure relates to a water purifier, and more particularly, to a water purifier having improved hygiene and improved convenience through a structure capable of horizontal displacement of a water outlet through which purified water generated by filtering raw water is discharged.

2. Discussion of Related Art

Water purifies are devices for generating purified water by filtering raw water supplied from the outside. In recent years, space efficiency at installation is considered as an important factor in selecting the water purifiers, and accordingly, undersink water purifiers and countertop water purifiers are widely used. In general, the undersink water purifiers and the countertop water purifiers have structures which are directly connected to pipes to which the raw water (for example, tap water) is supplied, and in which the raw water is filtered while passing through filters by water pressure, and is generated into the purified water, and the purified water is discharged to the outside through faucets.

In relation to such undersink water purifiers and such countertop water purifiers, research and development (R&D) for improving convenience, hygiene, and space efficiency of a water outlet is being actively conducted. Korean Patent Publication No. 2018-0063657 of AEON Co., Ltd. discloses an undersink purifier faucet that may selectively discharge purified water, cold water, and hot water through one faucet by user's operation because a touch-type operation unit is integrally formed in a faucet. Further, Korean Patent Publication No. 2021-0096346 of Samsung Electronics Co., Ltd. discloses a water purifier capable of variously changing a position of a water outlet portion.

The water outlet portion of the water purifier disclosed in the above related documents is provided rotatably in a predetermined range. However, the water outlet portion illustrated in the above related documents is always exposed to the outside, has a structure in which linear displacement is impossible, and thus has a limit in terms of convenience, hygiene, and space efficiency.

Meanwhile, Korean Patent No. 2064180 of Coway Co., Ltd. discloses a water discharge device having a structure in which a water outlet portion for outputting purified water is vertically movable. However, the water outlet portion disclosed in the related document is vertically movable but has a shape in which linear displacement in a horizontal direction is impossible, and thus has a limitation effect in securing convenience, hygiene, and space efficiency.

RELATED ART DOCUMENT

Patent Document (Patent Document 1) Korean Patent Publication No. 2018-0063657
(Patent Document 2) Korean Patent Publication No. 2021-0096346
(Patent Document 3) Korean Patent No. 2021-2064180

SUMMARY

In order to solve the above problems, a water purifier according to the present disclosure is configured such that a water outlet part may be displaced in a horizontal direction and the water outlet part may be exposed to the outside only when water is discharged, thereby improving hygiene, convenience, and space efficiency.

The water purifier according to an embodiment of the present disclosure allows the water outlet part to be displaced without interference with a driving part, thereby improving displacement efficiency of the water outlet part.

The water purifier according to the embodiment of the present disclosure allows the water outlet part to be displaced through a plurality of link water outlet flow paths without stretching and contracting or folding of each flow path member, thereby improving displacement efficiency, durability, and hygiene of the water outlet part.

The water purifier according to the embodiment of the present disclosure efficiently achieves horizontal displacement of the water outlet part through a rack and pinion structure.

The water purifier according to the embodiment of the present disclosure improves hygiene through a structure that may directly irradiate a water outlet port of the water outlet part with ultraviolet rays.

The water purifier according to the embodiment of the present disclosure improves usability through an interface unit that is integrally displaced together with the water outlet part.

The water purifier according to the embodiment of the present disclosure allows the plurality of link water outlet flow paths included in the water outlet part to be stably displaced through a link stabilization member.

A water purifier according to the present disclosure includes a water purification module that filters raw water to generate purified water, and a water outlet module that receives the purified water from the water purification module and outputs the purified water to the outside, wherein the water outlet module includes a housing, a purified water inlet flow path of which at least a portion is disposed inside the housing and into which the purified water is introduced, a movable part disposed to be displaced between a first position in which the movable part is retracted into the housing and a second position in which the movable part is extracted to a front side of the housing, a driving part that displaces the movable part, and a water outlet part that includes a plurality of link water outlet flow paths rotatably connected to each other and is connected to the movable part to receive the purified water from the purified water inlet flow path and discharge the purified water to an outside through the plurality of link water outlet flow paths, and the plurality of link water outlet flow paths of the water outlet part are unfolded when the movable part is displaced from the first position to the second position, the plurality of link water outlet flow paths of the water outlet part are folded when the movable part is displaced from the second position to the first position, and the water outlet part discharges the purified water to a lower side of the movable part when the movable part is located in the second position.

The driving part may be disposed above the water outlet part.

The movable part may move only in a horizontal direction when being displaced, and when the movable part is displaced, the plurality of link water outlet flow paths of the water outlet part are unfolded or folded with both a horizontal movement component and a vertical movement component.

The movable part may include a plate having a water outlet hole and disposed below the movable part, and a water outlet end of the water outlet part through which the purified water is discharged may be fixed to the water outlet hole, and a water inlet end of the water outlet part may be fixed to the purified water inlet flow path.

The driving part may include a motor fixed to the housing, a pinion coupled to an output shaft of the motor, and a rack bar coupled to the movable part, engaged with the pinion, and linearly moving forward or rearward according to rotation of the pinion.

The water purifier may further include an ultraviolet ray irradiation unit that is installed inside the housing such that the water outlet end of the water outlet part is positioned on an upper side when the movable part is located in the first position and irradiates the water outlet end of the water outlet part with ultraviolet rays.

The water purifier may further include an interface unit that is coupled to a front surface of the movable part, provides an operation interface, and is displaced integrally with the movable part.

The water outlet part may include a first link water outlet flow path connected to the purified water inlet flow path, a second link water outlet flow path having a first shaft pipe rotatably connected to the first link water outlet flow path, a second shaft pipe spaced apart from the first shaft pipe and arranged side by side, and a connection pipe connecting the first shaft pipe and the second shaft pipe, a third link water outlet flow path rotatably coupled to the second shaft pipe, and a fourth link water outlet flow path having a third shaft pipe to which the third link water outlet flow path is rotatably connected and a water outlet pipe extending outward from an outer surface of the third shaft pipe.

When the movable part is located in the first position, the first shaft pipe may be disposed in front of the second shaft pipe, and thus the third link water outlet flow path may be disposed in a stacked from with the first link water outlet flow path, and when the movable part is displaced from the first position to the second position, the second shaft pipe may rotate about the first shaft pipe in front of the first shaft pipe.

The first link water outlet flow path may be connected to one side of the first shaft pipe in an axial direction, the third link water outlet flow path may be connected to sides of the second shaft pipe and the third shaft pipe in the axial direction, and the other sides of the first to third axial shaft pipes in the axial direction may be closed.

The water outlet part may further include a first link stabilization member connected to the other side of the first shaft pipe in the axial direction to support the first shaft pipe, and a second link stabilization member connected to the other sides of the second shaft pipe and the third shaft pipe in the axial direction to support the second shaft pipe and the second shaft pipe.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
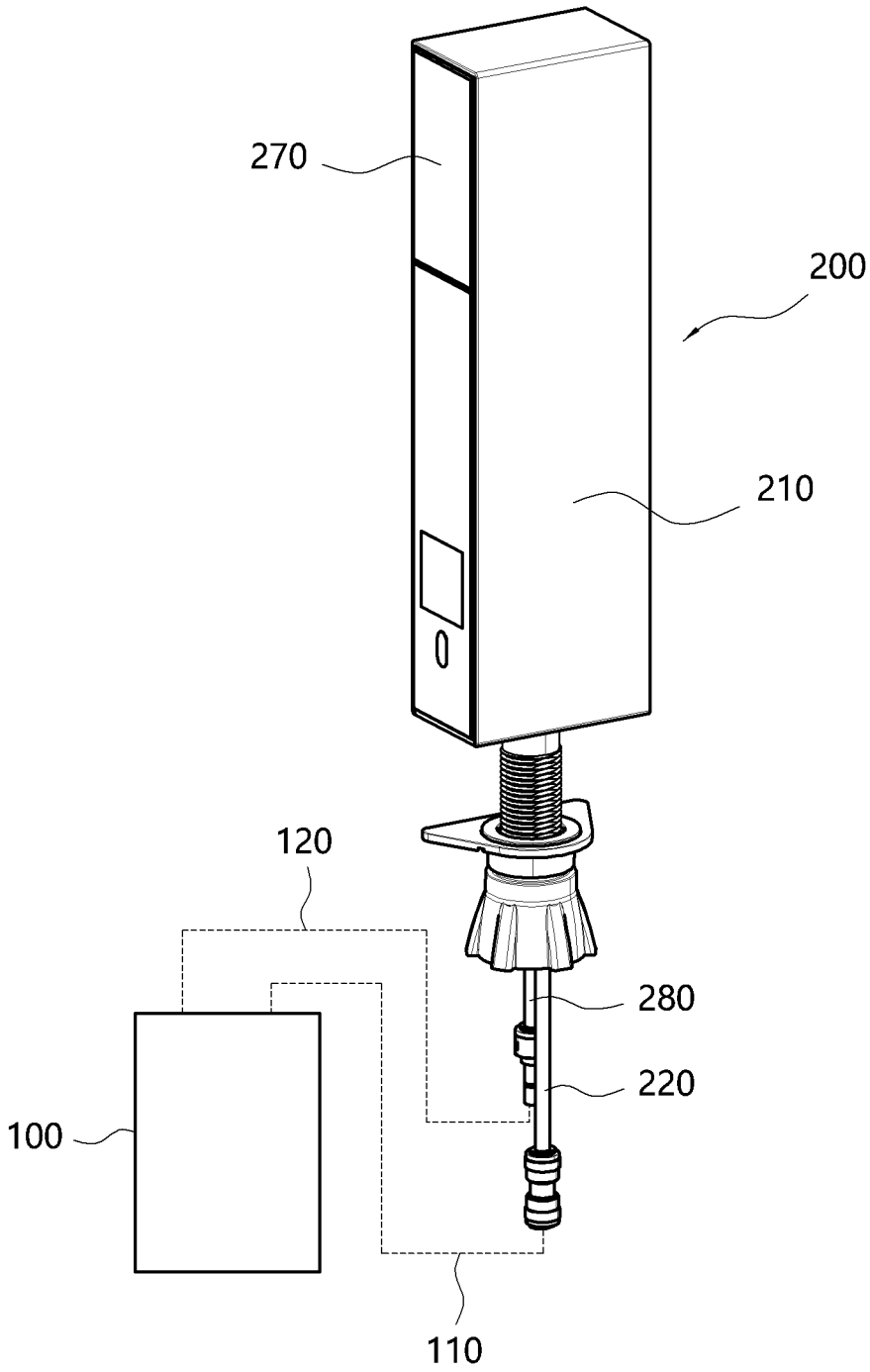
FIG. 1 is a diagram of a water purifier according to an embodiment of the present disclosure.

Terms or words used in the present specification and the appended claims are not limitedly interpreted as usual or dictionary meanings and should be interpreted as meanings and concepts corresponding to the technical spirit of the present disclosure based on the principle that the inventor may appropriately define the concepts of the terms in order to describe his/her disclosure in the best way.

Since the embodiments described in the present specification and configurations illustrated in the drawings correspond to the exemplary embodiments of the present disclosure and do not represent all the technical spirit of the present disclosure, the corresponding configurations may have various equivalents and modifications to replace them at a time of filing the present disclosure.

It should be understood in the present specification that the terms "include" or "have" are intended to describe that there are features, numbers, steps, operations, components, parts, or combinations thereof that are described in the specification and do not exclude in advance the possibility of the presence or addition of one or more other features, numbers, steps, operations, components, parts, or combinations thereof.

A case in which a component is present on a "front side," a "rear side," an "upper side," or a "lower side" of another component includes a case in which the component is disposed on the "front side," the "rear side," the "upper side," or the "lower side" in direct contact with the another component as well as a case in which still another component is disposed therebetween, unless otherwise specified.

Further, a case in which a first component is "connected" to a second component includes a case in which the first component and the second component are indirectly connected to each other as well as a case in which the first component and the second component are directly connected to each other unless otherwise specified.

Hereinafter, a water purifier according to an embodiment of the present disclosure will be described with reference to the accompanying drawings.

Figure 2:
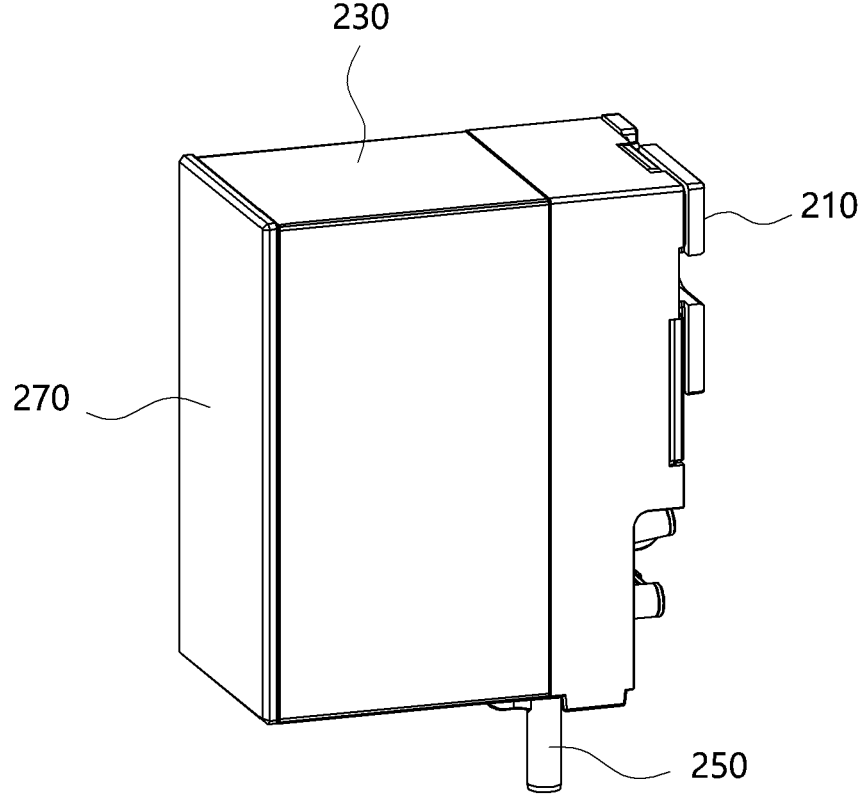
FIG. 2 is a view illustrating a partial configuration of a water outlet module of the water purifier according to the embodiment of the present disclosure.
Figure 3:
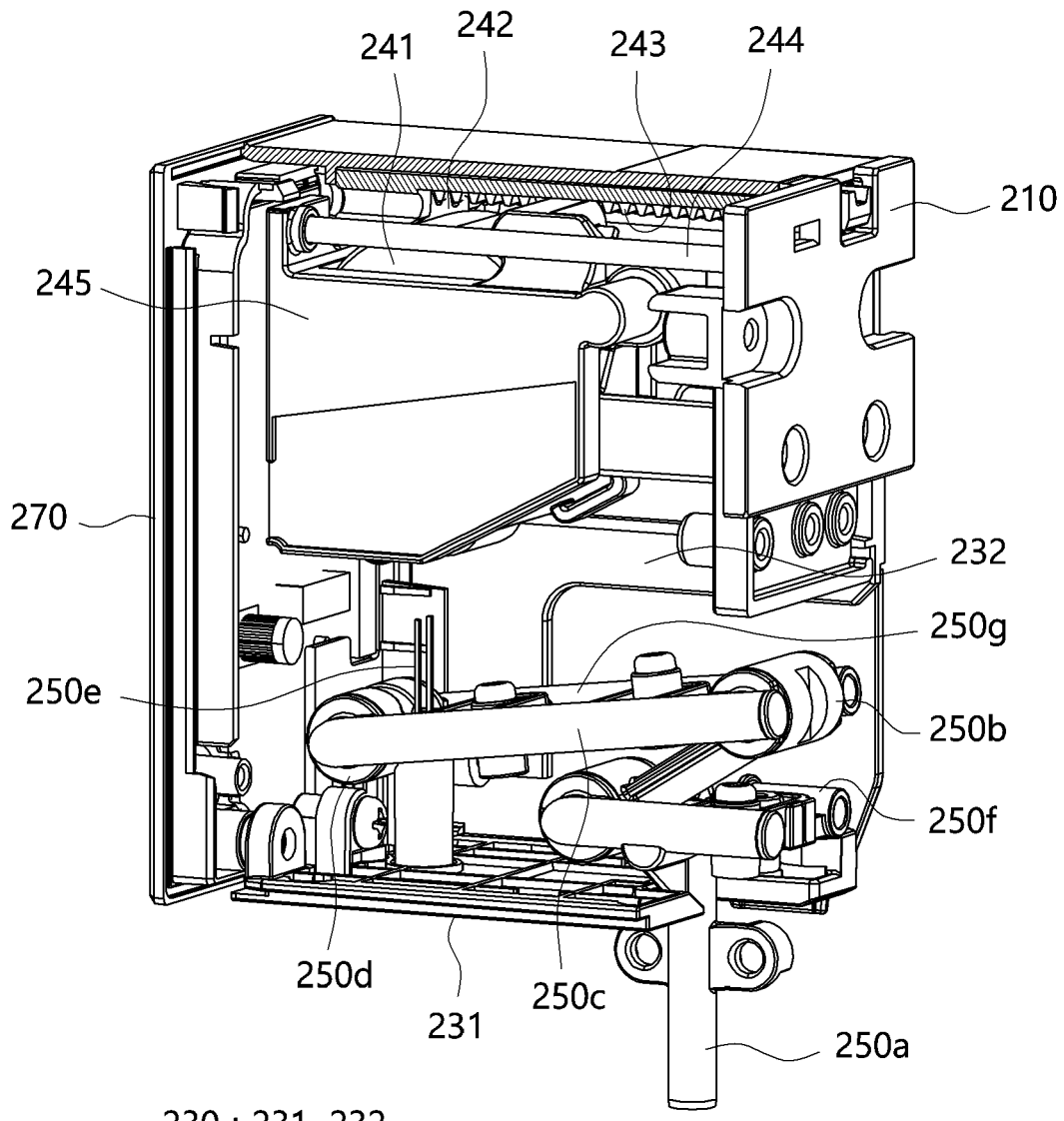
FIG. 3 is a view illustrating a state in which one side of a movable part is open in FIG. 2.
Figure 4:
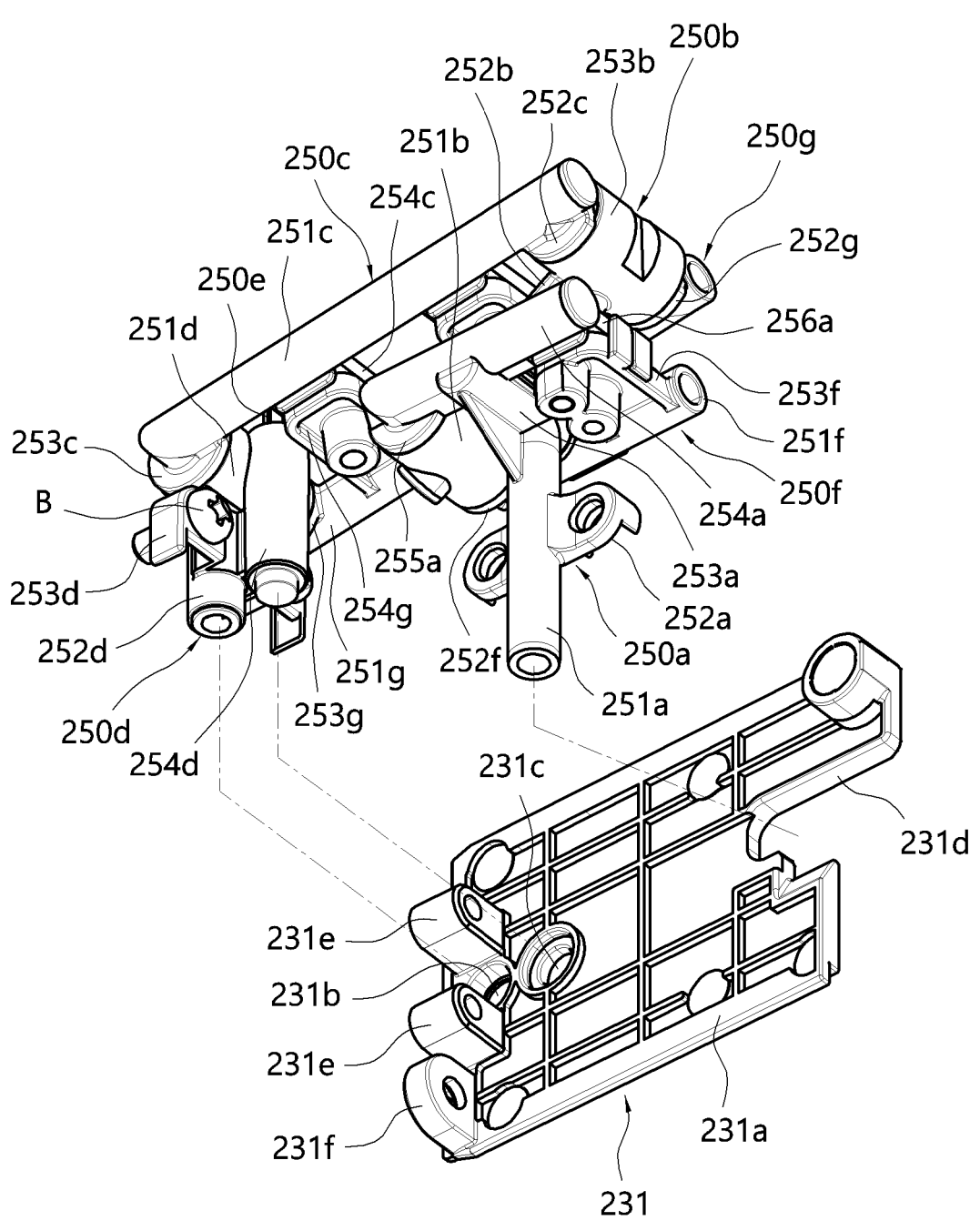
FIG. 4 is a view illustrating a state in which a plate and a water outlet portion of the movable part of the water purifier according to the embodiment of the present disclosure are separated from each other.
Figure 5:
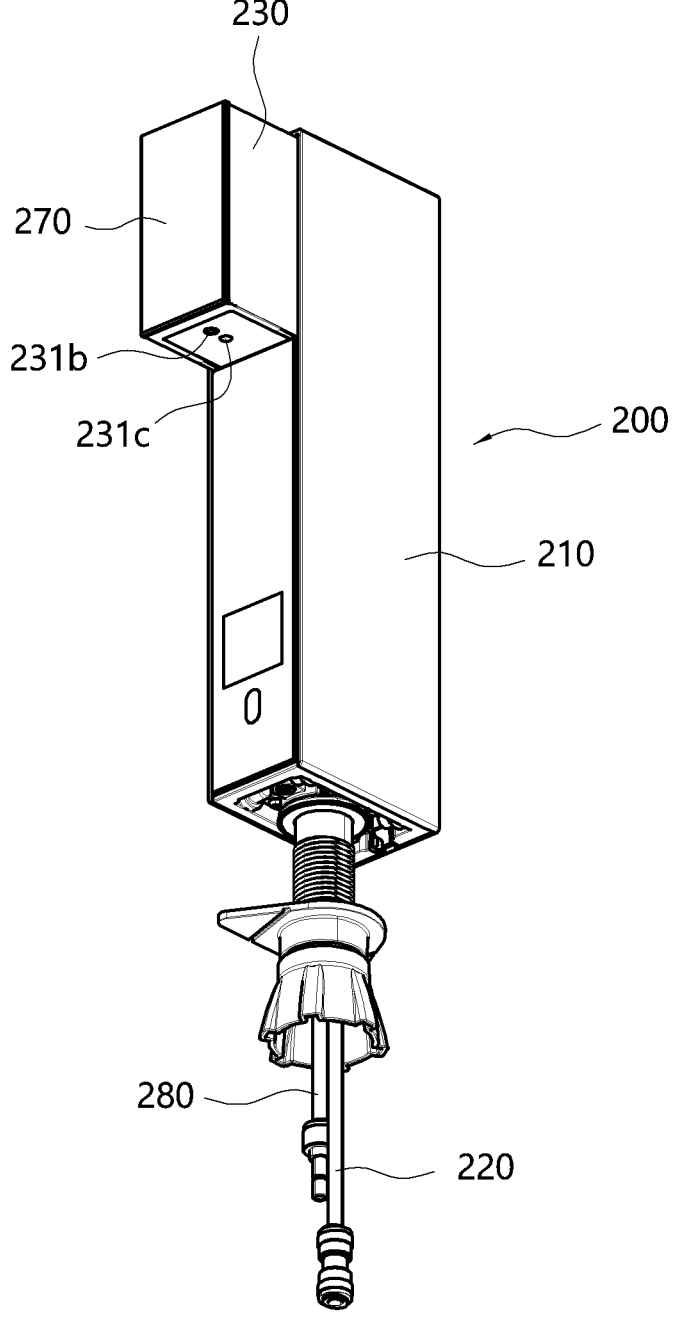
FIG. 5 is a view illustrating the water outlet module of the water purifier according to the embodiment of the present disclosure in a state in which the movable part is displaced forward.
Figure 6:
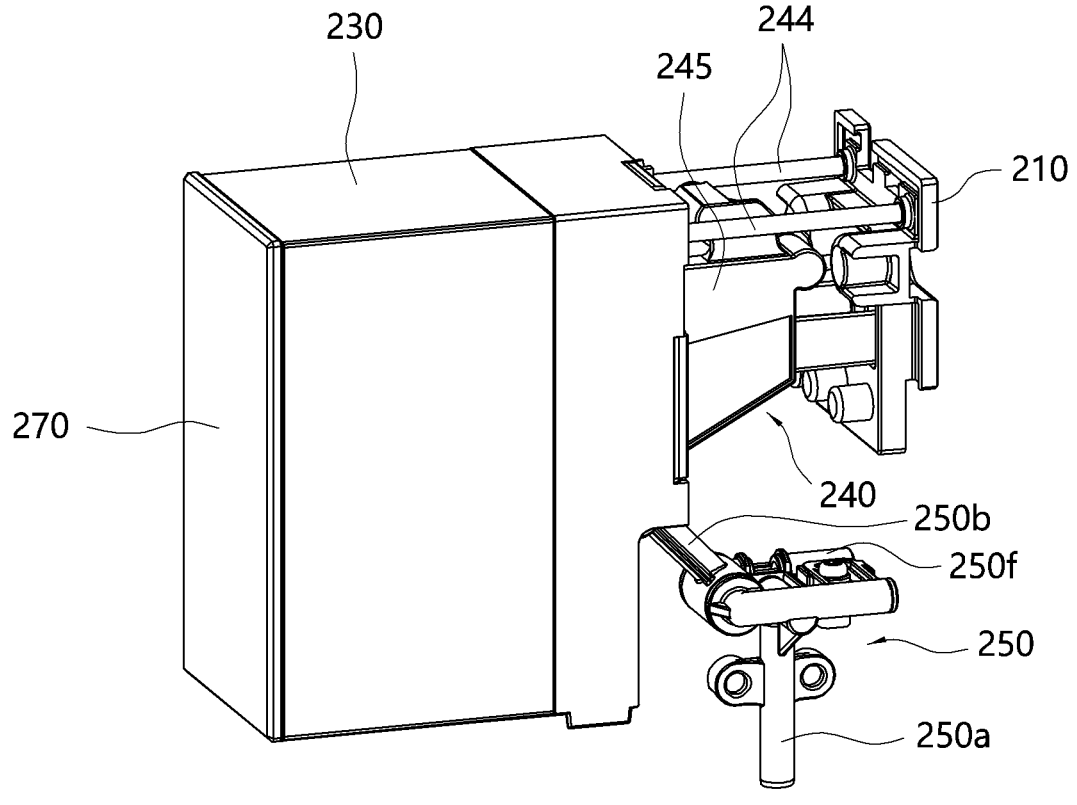
FIG. 6 is a view illustrating a partial configuration of the water outlet module of the water purifier according to the embodiment of the present disclosure in a state in which the movable part is displaced forward.
Figure 7:
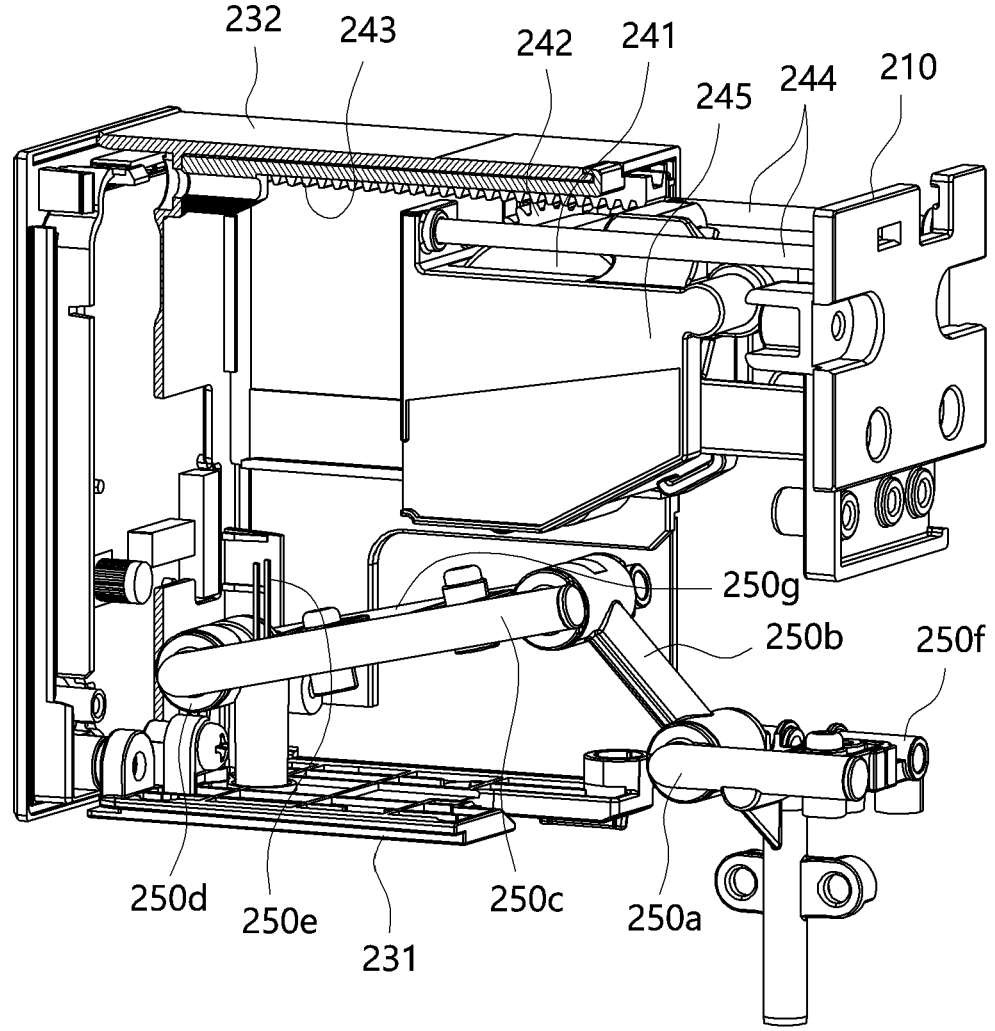
FIG. 7 is a view illustrating a state in which one side of the movable part is open in FIG. 6.
Figure 8:
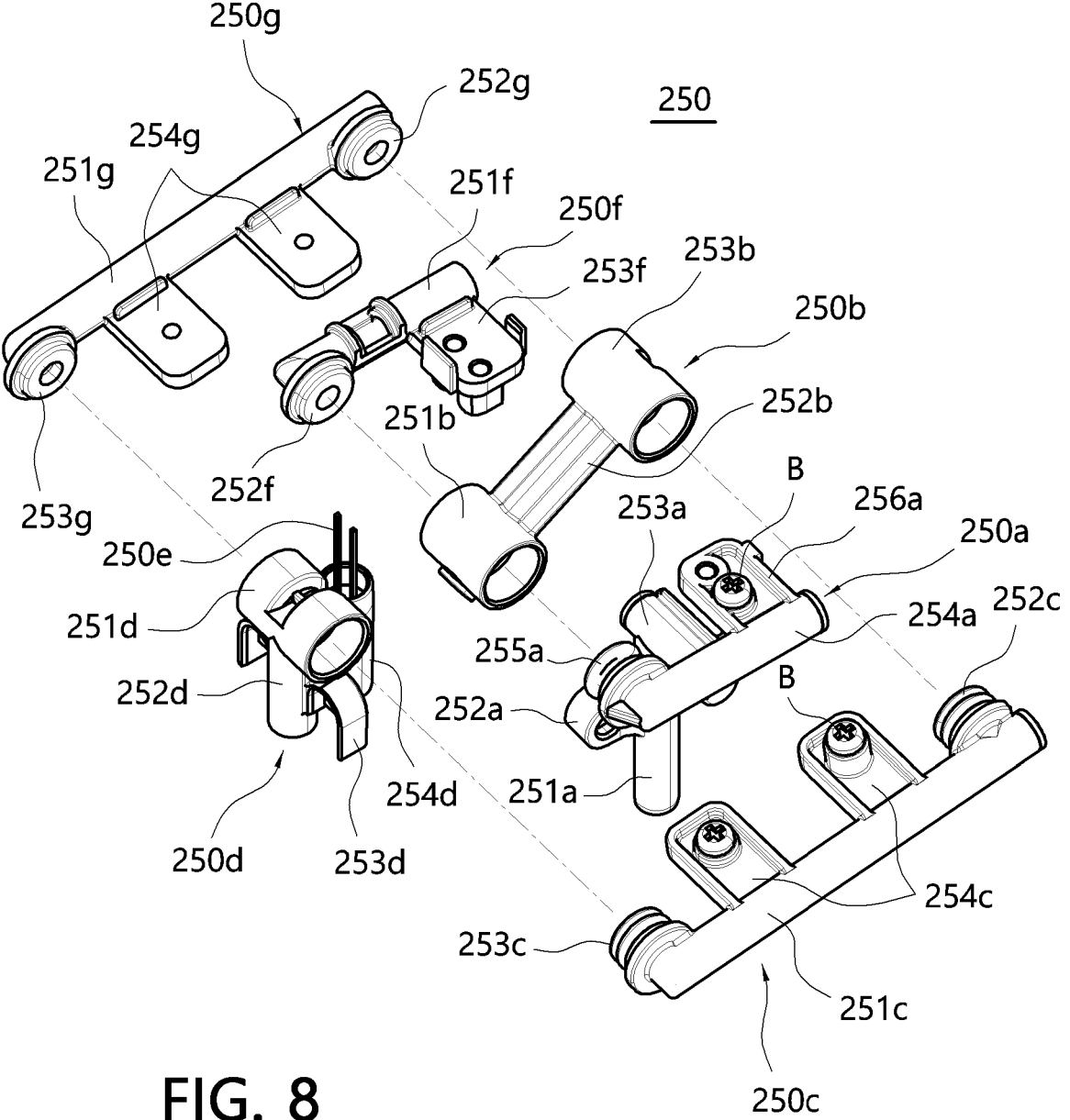
FIG. 8 is an exploded perspective view of the water outlet portion of the water purifier according to the embodiment of the present disclosure.
Figure 9:
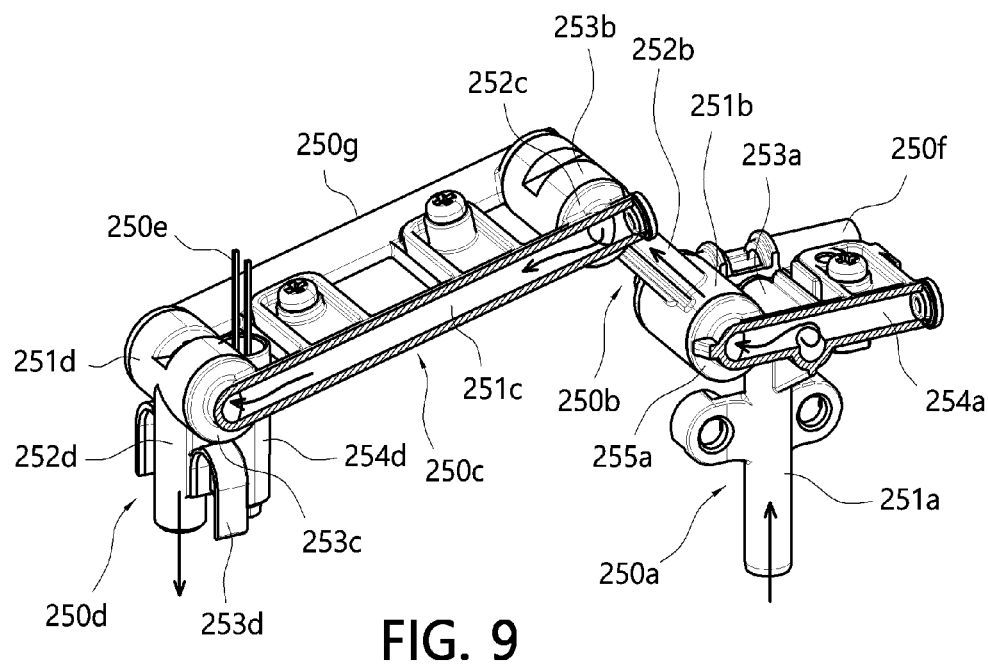
FIG. 9 is a view illustrating water output flow in the water outlet portion of the water purifier according to the embodiment of the present disclosure.
Figure 10:
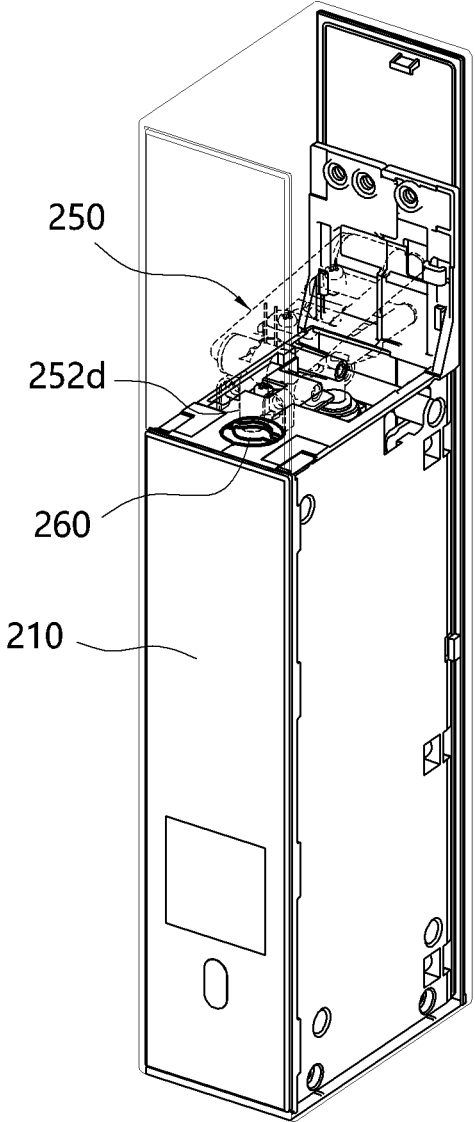
FIG. 10 is a view illustrating the water outlet module of the water purifier according to the embodiment of the present disclosure in a state in which the partial configuration is removed.

FIG. 1 is a diagram of a water purifier according to an embodiment of the present disclosure. FIG. 2 is a view illustrating a partial configuration of a water outlet module of the water purifier according to the embodiment of the present disclosure, and FIG. 3 is a view illustrating a state in which one side of a movable part is open in FIG. 2. Further, FIG. 4 is a view illustrating a state in which a plate and a water outlet portion of the movable part of the water purifier according to the embodiment of the present disclosure are separated from each other. FIG. 5 is a view illustrating the water outlet module of the water purifier according to the embodiment of the present disclosure in a state in which the movable part is displaced forward, FIG. 6 is a view illustrating a partial configuration of the water outlet module of the water purifier according to the embodiment of the present disclosure in a state in which the movable part is displaced forward, and FIG. 7 is a view illustrating a state in which one side of the movable part is open in FIG. 6. Meanwhile, FIG. 8 is an exploded perspective view of the water outlet portion of the water purifier according to the embodiment of the present disclosure, and FIG. 9 is a view illustrating water output flow in the water outlet portion of the water purifier according to the embodiment of the present disclosure. Further, FIG. 10 is a view illustrating the water outlet module of the water purifier according to the embodiment of the present disclosure in a state in which the partial configuration is removed.

Referring to FIGS. 1 to 10, a water purifier according to the embodiment of the present disclosure includes a water purification module 100 and a water outlet module 200.

The water purification module 100 filters raw water to generate purified water. The water purification module 100 may include a filter part (not illustrated) that filters the raw water. The water purification module 100 may be disposed separately from the water outlet module 200. For example, the water purification module 100 may be disposed below a sink. That is, the water purifier according to the embodiment of the present disclosure may be an under sink-type water purifier. Meanwhile, the water purification module 100 may be disposed to be coupled to the water outlet module 200. For example, the water purifier according to the embodiment of the present disclosure may be a countertop-type water purifier.

The water purification module 100 may include a water outlet flow path 110 through which the purified water is discharged toward the water outlet module 200 and a water inlet flow path 120 into which a fluid discharged from the water outlet module 200 flows. Further, the water purification module 100 may further include a cold water generation unit (not illustrated) that cools the purified water to generate cold water and a hot water generation unit (not illustrated) that heats the purified water to generate hot water. The cold water generated by the cold water generation unit and the hot water generated by the hot water generation unit may be discharged toward the water outlet module 200 through the water outlet flow path 110. In this regard, the water purification module 100 may further include a valve (not illustrated) through which the purified water, the cold water, and the hot water selectively flow to the water outlet flow path 110.

The water outlet module 200 receives the purified water from the water purification module 100 and outputs the received purified water to the outside. As described above, the water outlet module 200 may be disposed to be separated from the water purification module 100 or disposed to be coupled to the water purification module 100. In the embodiment of the present disclosure, the water outlet module 200 includes a housing 210, a purified water inlet flow path 220, a movable part 230, a driving part 240, a water outlet part 250, an ultraviolet ray irradiation unit 260, an interface unit 270, and a drainage flow path 280.

The housing 210 forms an exterior of the water outlet module 200. The purified water inlet flow path 220, the movable part 230, the driving part 240, the water outlet part 250, the ultraviolet ray irradiation unit 260, the interface unit 270, the drainage flow path 280, and the like are arranged in the housing 210. For example, the housing 210 may have a quadrangular pole shape.

The purified water inlet flow path 220 is configured such that the purified water flows thereinto. At least a portion of the purified water inlet flow path 220 may be disposed inside the housing 210. One end of the purified water inlet flow path 220 may be connected to the water outlet flow path 110 of the water purification module 100, and the other end of the purified water inlet flow path 220 may be connected to the water outlet part 250. In the embodiment of the present disclosure, the purified water inlet flow path 220 may vertically extend such that the purified water flows from a lower side to an upper side of the water outlet module 200.

The movable part 230 may be displaced between a first position in which the movable part 230 is retracted into the housing 210 and a second position in which the movable part 230 is extracted to a front side of the housing 210. The movable part 230 may be displaced in a horizontal direction between the first position and the second position. Further, in the embodiment of the present disclosure, the movable part 230 may be disposed above the housing 210. Referring to FIGS. 3 and 4, the movable part 230 includes a plate 231 and a movable part housing 232.

The plate 231 has a water outlet hole 231b and is disposed below the movable part 230. That is, the plate 231 is disposed to define a lower portion of the movable part 230. Referring to FIG. 5, when the movable part 230 is disposed at the second position in which the movable part 230 is extracted to the front side of the housing 210, the plate 231 may be exposed to the outside of the housing 210, and the purified water may be discharged through the water outlet hole 231b.

Referring to FIG. 4, the plate 231 includes a plate body 231a, the water outlet hole 231b formed to pass through the plate body 231a, an illumination hole 231c formed to pass through the plate body 231a so that an illumination light proceeds to the outside, a recessed part 231d recessed forward in a rear portion of the plate body 231 for arrangement of a first link water outlet flow path 250a of the water outlet part 250, which will be described below, a first plate fastening part 231e protruding and extending upward from a front portion of the plate body 231a for fastening with the water outlet part 250, and a second plate fastening part 231f protruding and extending upward from the front portion of the plate body 231a for fastening with the movable part housing 232. In this case, a water outlet end of the water outlet part 250 may be fixed to the water outlet hole 231a.

Further, the first fastening part 231$e$ may be fastened to a fourth link water outlet flow path 250$d$ of the water outlet part 250.

The movable part housing 232 is disposed to cover both side surfaces, an upper surface, and a front surface of the movable part 230. In other words, the movable part housing 232 partitions both side surfaces, the upper surface, and the front surface of the movable part 230. The movable part housing 232 may be coupled to the plate 231. In the embodiment of the present disclosure, the movable part 230 may have a box shape have an open rear side by the movable part housing 232 and the plate 231.

In a state in which the movable part 230 is disposed in the first position, the water outlet hole 231$b$ of the plate 231 is not exposed to the outside of the water outlet module 200, and in a state in which the movable part 230 is disposed in the second position, the water outlet hole 231$b$ of the plate 231 is exposed to the outside of the water outlet module 200. Thus, according to the present disclosure, the water outlet hole 231$b$ is not always exposed to the outside, and the water outlet hole 231$b$ may be exposed to the outside only when the purified water is to be discharged. Accordingly, the hygiene and space efficiency of the water purifier can be increased.

The driving part 240 displaces the movable part 230. The driving part 240 displaces the movable part 230 from the first position in which the movable part 230 is retracted into the housing 210 to the second position in which the movable part 230 is extracted to the front side of the housing 210 or displaces the movable part 230 from the second position in which the movable part 230 is extracted to the front side of the housing 210 or the first position in which the movable part 230 is retracted into the housing 210.

In the embodiment of the present disclosure, the driving part 240 is disposed above the water outlet part 250. When the movable part 230 is displaced between the first position and the second position in the horizontal direction, the water outlet part 250 has both a horizontal movement component and a vertical movement component. However, in the embodiment of the present disclosure, the water outlet part 250 is coupled to the plate 231 defining a lower portion of the movable part 230. Thus, when the driving part 240 is disposed above the water outlet part 250, the water outlet part 250 may be smoothly displaced without interference with the driving part 240.

Referring to FIGS. 3, 6, and 7, the driving part 240 includes a motor 241 fixed to the housing 210, a pinion 242 coupled to an output shaft of the motor 241, and a rack bar 243 that is coupled to the movable part 230, is engaged with the pinion 242, and linearly moves forward or rearward according to rotation of the pinion 242. In more detail, the driving part 240 may further include a fixed bar 244 having one end coupled to a portion of the housing 210, which covers an upper rear portion of the water outlet module 200 and having a form of a forwardly extending cantilever, and a motor housing 245 fastened to the fixed bar 244, wherein the motor 241 is disposed inside the motor housing 245. In this case, the fixed bar 244 may be provided as a plurality of fixed bars 244 arranged side by side. Meanwhile, the rack bar 243 may be coupled to the movable part housing 232. In the embodiment of the present disclosure, the rack bar 243 is coupled to a portion of the movable part housing 232, which covers an upper side of the movable part 230.

The water outlet part 250 receives the purified water from the purified water inlet flow path 220 and discharges the purified water to the outside. Referring to FIGS. 3, 4, and 6 to 8, the water outlet part 250 includes a plurality of link water outlet flow paths 250$a$, 250$b$, 250$c$, and 250$d$ rotatably connected to each other. The water outlet part 240 is connected to the movable part 230 to receive the purified water from the purified water inlet flow path 220 and discharge the purified water to the outside through the plurality of link water outlet flow paths 250$a$, 250$b$, 250$c$, and 250$d$. In this case, the water outlet end of the water outlet part 250, through which the purified water is discharged, is fixed to the water outlet hole 231$b$ of the movable part 230, and a water inlet end of the water outlet part 250 is fixed to the purified water inlet flow path 220.

The plurality of link water outlet flow paths 250$a$, 250$b$, 250$c$, and 250$d$ of the water outlet part 250 may be unfolded when the movable part 230 is displaced from the first position to the second position and may be folded when the movable part 230 is displaced from the second position to the first position. Further, when the movable part 230 is located at the second position, the water outlet part 250 may discharge the purified water to the lower side of the movable part 230.

As described above, the movable part 230 moves only in the horizontal direction when displaced. On the other hand, the plurality of link water outlet flow paths 250$a$, 250$b$, 250$c$, and 250$d$ of the water outlet part 250 are unfolded or folded with both a horizontal movement component and a vertical movement component when the movable part 230 is displaced.

In the embodiment of the present disclosure, the water outlet part 250 includes the first link water outlet flow path 250$a$, the second link water outlet flow path 250$b$, the third link water outlet flow path 250$c$, and the fourth link water outlet flow path 250$d$.

The first link water outlet flow path 250$a$ is connected to the purified water inlet flow path 220. In the embodiment of the present disclosure, the first link water outlet flow path 250$a$ includes a $(1\text{-}1)^{th}$ link flow path member 251$a$ having a lower end connected to the purified water inlet flow path 220 and vertically extending, a link flow path fastening part 252$a$ extending outward from an outer surface of the $(1\text{-}1)^{th}$ link flow path member 251$a$ such that a fastening member that fastens the first link water outlet flow path 250$a$ to the housing 210 is coupled thereto, a $(1\text{-}2)^{th}$ link flow path member 253$a$ connected in fluid communication with an upper end of the $(1\text{-}1)^{th}$ link flow path member 251$a$, a $(1\text{-}3)^{th}$ link flow path member 254$a$ connected in fluid communication with the $(1\text{-}2)^{th}$ link flow path member 253$a$ and extending in a front-rear direction, a first connection part 255$a$ provided at a front end of the $(1\text{-}3)^{th}$ link flow path member 254$a$ for connection with the second link water outlet flow path 250$b$, and a first extension part 256$a$ extending outward from an outer surface of the $(1\text{-}3)^{th}$ link flow path member 254$a$ for fastening with a first link stabilization member 250$f$ which will be described below.

The second link water outlet flow path 250$b$ includes a first shaft pipe 251$b$ rotatably connected to the first link water outlet flow path 250$a$, a second shaft pipe 253$b$ spaced apart from the first shaft pipe 251 and arranged side by side, and a connection pipe 252$b$ connecting the first shaft pipe 251$b$ and the second shaft pipe 253$b$. In the embodiment of the present disclosure, the first shaft pipe 251$b$ and the second shaft pipe 253$b$ each function as a rotary shaft and arranged parallel to each other. Further, the first shaft pipe 251$b$ and the second pipe 253$b$ may be arranged to extend in a left-right direction. The first link water outlet flow path 250$a$ may be connected to one side of the first shaft pipe 251$b$ in an axial direction. In more detail, in the embodiment of the present disclosure, the first connection part 255$a$ of the first link water outlet flow path 250*a* is connected to the one side of the first shaft pipe 251*b* in the axial direction while ensuring watertightness. The other side of the first shaft pipe 251*b* in the axial direction is closed, and the connection pipe 252*b* connects a side portion of the first shaft pipe 251*b* and the second shaft pipe 253*b*. Further, similar to the first shaft pipe 251*b*, the other side of the second shaft pipe 253*b* in the axial direction is also closed, and one side of the second shaft pipe 253*b* in the axial direction communicates with the third link water outlet flow path 250*c*.

The third link water outlet flow path 250*c* is rotatably coupled to the second shaft pipe 253*b*. In the embodiment of the present disclosure, the third link water outlet flow path 250*c* includes a third link flow path member 251*c* disposed to allow the purified water supplied from the second link water outlet flow path 250*b* to flow into the fourth link water outlet flow path 250*d*. The third link flow path member 251*c* extends in a front-rear direction. The third link water outlet flow path 250*c* further includes a second connection part 252*c* provided at a rear end of the third link flow path member 251*c*, a third connection part 253*c* provided at a front end of the third link flow path member 251*c*, and a second extension part 254*c* extending outward from an outer surface of the third link flow path member 251*c* for fastening with a second link stabilization member 250*g*. The second extension part 254*c* may be provided as a plurality of second extension parts 254*c*. Further, the second connection part 252*c* is connected to one side of the second shaft pipe 253*b* of the second link water outlet flow path 250*b* in the axial direction while ensuring watertightness.

The fourth link water outlet flow path 250*d* includes a third shaft pipe 251*d* to which the third link water outlet flow path 250*c* is rotatably coupled and a water outlet pipe 252*d* extending outward from an outer circumferential surface of the third shaft pipe 251*d*. The third shaft pipe 251*d* may function as a rotary shaft and may be disposed to extend in a left-right direction. The third connection part 253*c* of the third link water outlet flow path 250*c* is connected to one side of the third shaft pipe 251*d* in the axial direction while ensuring watertightness. The other side of the third shaft pipe 251*d* in the axial direction may be closed, and the purified water flowing to the third shaft pipe 251*d* may be discharged to the outside through the water outlet pipe 252*d*. Further, the water outlet pipe 252*d* may extend downward from the third shaft pipe 251*d*. In the embodiment of the present disclosure, the water outlet pipe 252*d* is connected to the plate 231 of the movable part 230. In more detail, a water outlet end of the water outlet pipe 252*d* may be fitted into the water outlet hole 231*b* of the plate 231. Further, the fourth link water outlet flow path 250*d* includes a third connection part 253*d* extending outward from an outer side of the water outlet pipe 252*d* such that a fastening member for fastening the water outlet pipe 252*d* to the first plate fastening part 231*e* is fastened thereto. Since the fastening member (for example, a screw) is fastened to the first plate fastening part 231*e* while passing through the third connection part 253*d*, the plate 231 and the fourth link water outlet flow path 250*d* may be fastened to each other. Meanwhile, the fourth link water outlet flow path 250*d* may further include a light source arrangement part 254*d* extending side by side with the water outlet pipe 252*d* on the outer surface of the third shaft pipe 251*d*. An end of the light source arrangement part 254*d* is fastened to the illumination hole 231*c* of the plate 231 such that the illumination light passes therethrough. A light source 250*e* may be disposed inside the light source arrangement part 254*d*, and when the purified water is discharged through the water discharge hole 231*b*, the illumination light by the light source 250*e* may be provided through the illumination hole 231*c*.

Referring to FIGS. 3, 7, and 8, when the movable part 230 is located in the first position, the first shaft pipe 251*b* is disposed in front of the second shaft pipe 253*b*, and the third link water outlet flow path 250*c* is disposed in a form stacked with the first link water outlet flow path 250*a*. Further, when the movable part 230 is displaced from the first position to the second position, the second shaft pipe 253*b* rotates to a front side of the first shaft pipe 251*b* about the first shaft pipe 251*b*. In this way, in the embodiment of the present disclosure, when the movable part 230 is displaced between the first position and the second position in the horizontal direction, the water outlet part 250 is displaced with both a horizontal movement component and a vertical movement component to allow the water to be discharged from the outside of the housing 210. In other words, the water outlet part 250 may be displaced in the horizontal direction without stretching and contracting or folding of the individual flow path members through the plurality of link water outlet flow paths 250*a*, 250*b*, 250*c*, and 250*d*. Therefore, the hygiene of the water outlet part 250 may be improved. Further, the durability of the water outlet part 250 may be secured.

Referring to FIG. 9, the purified water introduced into the water outlet part 250 through the first link flow path member 251*a* flows to the third link water outlet flow path 250*c* via the first shaft pipe 251*b*, the connection pipe 252*b*, and the second shaft pipe 253*b* of the second link water outlet flow path 250*b*. Further, the purified water passing through the third link water outlet flow path 250*c* is discharged to the outside via the third shaft pipe 251*d* and the water outlet pipe 252*d* of the fourth link water outlet flow path 250*d*. Prior to formation of these flow paths, as described above, the first link water outlet flow path 250*a* is connected to the one side of the first shaft pipe 251*b* in the axial direction, and the third link water outlet flow path 250*c* is connected to sides of the second shaft pipe 253*b* and the third shaft pipe 251*d* in the axial direction. Further, the other sides of the first shaft pipe 251*b*, the second shaft pipe 253*b*, and the third shaft pipe 251*d* in the axial direction are closed.

Meanwhile, the water outlet part 250 may further include the first link stabilization member 250*f* connected to the other side of the first shaft pipe 251*b* in the axial direction to support the first shaft pipe 251*b* and the second link stabilization member. 250*g* connected to the other sides of the second shaft pip 253*b* and the third shaft pipe 251*d* in the axial direction to support the second shaft pipe 253*b* and the third shaft pipe 251*d*. The stability of rotational displacement of the water outlet part 250 can be increased through the first link stabilization member 250*f* and the second link stabilization member 250*g*.

The first link stabilization member 250*f* together with the first link water outlet flow path 250*a* supports the first shaft pipe 251*b* of the second link water outlet flow path 250*b*. In the embodiment of the present disclosure, the first link stabilization member 250*f* may include a first link bar 251*f* disposed in parallel to the $(1\text{-}3)^{th}$ link flow path member 254 of the first link water outlet flow path 250*a*, a fourth connection part 252*f* provided at a front end of the first link bar 251*f* and connected to the other side of the first shaft pipe 251*b* in the axial direction, and a third extension part 253*f* extending outward from an outer surface of the first link bar 251*f* so that a fastening member B disposed to pass through the first extension part 256*a* while overlapping the first extension part 256*a* is fastened thereto.

The second link stabilization member 250*g* together with the third link water outlet flow path 250*c* supports the third shaft pipe 251*d* of the fourth link water outlet flow path 250*d*. Further, the second link stabilization member 250*g* together with the third link water outlet flow path 250*c* may allow the second shaft pipe 253*b* to stably rotate about the first shaft pipe 251*b*. In the embodiment of the present disclosure, the second link stabilization member 250*g* may include a second link bar 251*g* disposed side by side with the third link flow path member 251*c* and rotating the second shaft pipe 253*b*, a fifth connection part 252*g* provided on an outer surface of a rear end of the second link bar 251*g* and connected to the other side of the second shaft pipe 253*b* in the axial direction, a sixth connection part 253*g* extending from an outer surface of a front end of the second link bar 251*g* and connected to the other side of the third shaft pipe 251*d* in the axial direction, and a fourth extension part 254*g* extending outward from the outer surface of the second link bar 251*g* so that the fastening member B disposed to pass through the second extension part 254*c* while overlapping the second extension part 254*c* is fastened thereto.

The ultraviolet ray irradiation unit 260 is installed inside the housing 210 such that the water outlet end of the water outlet part 250 is positioned on an upper side when the movable part 230 is located in the first position, and irradiates the water outlet end of the water outlet part 250 with ultraviolet rays. Referring to FIG. 10, when the movable part 230 is located in the first position, it may be identified that the water outlet end of the water outlet part 250, that is, an end of the water outlet pipe 252*d* of the fourth link water outlet flow path 250*d*, is disposed above the ultraviolet ray irradiation unit 260 (in FIG. 10, the plate 231 of the movable part 230 is not illustrated). In this way, according to the present disclosure, when the movable part 230 is located in the first position, the ultraviolet ray irradiation unit 260 may directly irradiate the water outlet end of the water outlet part 250 with ultraviolet rays, and therefore, the hygiene of the water purifier can be improved.

The interface unit 270 is coupled to a front surface of the movable part 230, provides an operation interface, and is displaced integrally with the movable part 230. The interface unit 270 may be coupled to a portion partitioning a front side of the movable part housing 232. For example, the interface unit 270 may provide a touch screen-type operation interface. Further, the interface unit 270 may display various pieces of information. According to the present disclosure, usability can be improved through the interface unit 270 integrally displaced together with the water outlet part 250.

The drainage flow path 280 is a flow path through which a fluid that needs to be drained without being discharged to the outside among a fluid provided through the purified water inlet flow path 220 is discharged to the water purification module 100. The drainage flow path 280 is connected to the water inlet flow path 120 of the water purification module 100. As described above, the water purification module 100 may provide the cold water or the hot water in addition to the purified water. When a user selects discharge of the hot water, the fluid in the purified water inlet flow path 220 may be drained through the drainage flow path 280 without being supplied to the water outlet part 250 until the hot water supplied from the water purification module 100 reaches a predetermined temperature. In this regard, a valve (not illustrated) may be disposed between the purified water inlet flow path 220 and the water outlet part 250, and the drainage flow path 280 may be connected to the valve.

According to the above configuration, a water purifier according to the present disclosure can be configured such that a water outlet part may be displaced in a horizontal direction and the water outlet part may be exposed to the outside only when water is discharged, thereby improving hygiene, convenience, and space efficiency.

The water purifier according to an embodiment of the present disclosure can allow the water outlet part to be displaced without interference with a driving part, thereby improving displacement efficiency of the water outlet part.

The water purifier according to the embodiment of the present disclosure can allow the water outlet part to be displaced through a plurality of link water outlet flow paths without stretching and contracting or folding of each flow path member, thereby improving displacement efficiency, durability, and hygiene of the water outlet part.

The water purifier according to the embodiment of the present disclosure can efficiently achieve horizontal displacement of the water outlet part through a rack and pinion structure.

The water purifier according to the embodiment of the present disclosure can improve hygiene through a structure that may directly irradiate a water outlet port of the water outlet part with ultraviolet rays.

The water purifier according to the embodiment of the present disclosure can improve usability through an interface unit that is integrally displaced together with the water outlet part.

The water purifier according to the embodiment of the present disclosure can allow the plurality of link water outlet flow paths included in the water outlet part to be stably displaced through a link stabilization member.

Although the embodiments of the present disclosure have been described above, the spirit of the present disclosure is not limited to the embodiments presented in the present specification. Those skilled in the art who understand the spirit of the present disclosure could easily propose other embodiments by adding, changing, deleting, adding, or the like of components within the same scope of the spirit. Further, these other embodiments also belong to the scope of the spirit of the present disclosure.

What is claimed is:

1. A water purifier comprising:
   a water purification module that filters raw water to generate purified water; and
   a water outlet module that receives the purified water from the water purification module and outputs the purified water to an outside of the water outlet module,
   wherein the water outlet module includes:
   a housing;
   a purified water inlet flow path of which at least a portion is disposed inside the housing and into which the purified water is introduced;
   a movable part disposed to be displaced between a first position in which the movable part is retracted into the housing and a second position in which the movable part is extracted to a front side of the housing;
   a driving part that displaces the movable part; and
   a water outlet part that includes a plurality of link water outlet flow paths rotatably connected to each other and is connected to the movable part to receive the purified water from the purified water inlet flow path and discharge the purified water to the outside of the water outlet module through the plurality of link water outlet flow paths,
   the plurality of link water outlet flow paths of the water outlet part are unfolded when the movable part is displaced from the first position to the second position, the plurality of link water outlet flow paths of the water outlet part are folded when the movable part is displaced from the second position to the first position, and the water outlet part discharges the purified water to a lower side of the movable part when the movable part is located in the second position, wherein the movable part includes a plate having a water outlet hole and disposed below the movable part, a water outlet end of the water outlet part through which the purified water is discharged is fixed to the water outlet hole, and a water inlet end of the water outlet part is fixed to the purified water inlet flow path, and when the movable part is disposed in the first position, the water outlet hole is not exposed to the outside of the water outlet module, when the movable part is disposed in the second position, the water outlet hole is exposed to the outside of the water outlet module.

2. The water purifier of claim 1, wherein the driving part is disposed above the water outlet part.

3. The water purifier of claim 1, wherein the movable part moves only in a horizontal direction when being displaced, and when the movable part is displaced, the plurality of link water outlet flow paths of the water outlet part are unfolded or folded with both a horizontal movement component and a vertical movement component.

4. The water purifier of claim 1, wherein the driving part includes: a motor fixed to the housing;

a pinion coupled to an output shaft of the motor; and a rack bar coupled to the movable part, engaged with the pinion, and linearly moving forward or rearward according to rotation of the pinion.

5. The water purifier of claim 1, further comprising an ultraviolet ray irradiation unit that is installed inside the housing such that the water outlet end of the water outlet part is positioned on an upper side when the movable part is located in the first position and irradiates the water outlet end of the water outlet part with ultraviolet rays.

6. The water purifier of claim 1, further comprising an interface unit that is coupled to a front surface of the movable part, provides an operation interface, and is displaced integrally with the movable part.

7. The water purifier of claim 1, wherein the water outlet part includes:

a first link water outlet flow path connected to the purified water inlet flow path;

a second link water outlet flow path having a first shaft pipe rotatably connected to the first link water outlet flow path, a second shaft pipe spaced apart from the first shaft pipe and arranged side by side, and a connection pipe connecting the first shaft pipe and the second shaft pipe;

a third link water outlet flow path rotatably coupled to the second shaft pipe; and a fourth link water outlet flow path having a third shaft pipe rotatably connected to the third link water outlet flow path and a water outlet pipe extending outward from an outer surface of the third shaft pipe.

8. The water purifier of claim 7, wherein, when the movable part is located in the first position, the first shaft pipe is disposed in front of the second shaft pipe, and thus the third link water outlet flow path is disposed in a stacked from with the first link water outlet flow path, and when the movable part is displaced from the first position to the second position, the second shaft pipe rotates about the first shaft pipe in front of the first shaft pipe.

9. The water purifier of claim 8, wherein the first link water outlet flow path is connected to one side of the first shaft pipe in an axial direction, the third link water outlet flow path is connected to sides of the second shaft pipe and the third shaft pipe in the axial direction, and the other sides of the first to third shaft pipes in the axial direction are closed.

10. The water purifier of claim 9, wherein the water outlet part further includes:

a first link stabilization member connected to the other side of the first shaft pipe in the axial direction to support the first shaft pipe; and a second link stabilization member connected to the other sides of the second shaft pipe and the third shaft pipe in the axial direction to support the second shaft pipe and the second shaft pipe.

* * * * *